US00PP30909P2

(12) United States Plant Patent
Hansen

(10) Patent No.: US PP30,909 P2
(45) Date of Patent: Sep. 24, 2019

(54) ***COREOPSIS* PLANT NAMED 'RED HOT VANILLA'**

(50) Latin Name: *Coreopsis verticillate*
Varietal Denomination: Red Hot Vanilla

(71) Applicant: Hans A Hansen, Zeeland, MI (US)

(72) Inventor: Hans A Hansen, Zeeland, MI (US)

(73) Assignee: Walters Gardens Inc, Zeeland, MI (US)

( * ) Notice: Subject to any disclaimer, the term of this patent is extended or adjusted under 35 U.S.C. 154(b) by 0 days.

(21) Appl. No.: 16/350,350

(22) Filed: Nov. 5, 2018

(51) Int. Cl.
*A01H 5/02* (2018.01)
*A01H 6/14* (2018.01)

(52) U.S. Cl.
USPC ..... Plt./417

(58) Field of Classification Search
USPC ..... Plt./417
CPC ..... A01H 5/02; A01H 6/14
See application file for complete search history.

*Primary Examiner* — Annette H Para

(57) ABSTRACT

The new and distinct threadleaf *coreopsis* plant, *Coreopsis verticillata* plant named 'Red Hot Vanilla', dense mounded habit, with narrowly-linear or deeply-dissected, typically 3-lobed foliage of bright-green, heavily-branched, producing numerous inflorescences with creamy ray ligules with dark red central eye over a prolonged flowering season from early summer until frost.

1 Drawing Sheet

Botanical designation: *Coreopsis verticillate.*
Cultivar denomination: 'Red Hot Vanilla'.

STATEMENT REGARDING PRIOR DISCLOSURES UNDER 37 CFR 1.77(b)(6)

The first public disclosure of the claimed plant, in the form of a sale, was made by Walters Gardens, Inc. on Jul. 9, 2018. Prior to that, on Nov. 28, 2017 the claimed plant was displayed as a photograph without description in a calendar distributed to customers of Walters Gardens, Inc., who obtained the plant and all information relating thereto, from the inventor. No plants of *Coreopsis* 'Red Hot Vanilla' have been sold, in this country or anywhere in the world, nor has any disclosure of the new plant been made, more than one year prior the filing date of this application, and such sale or disclosure within one year was either derived directly or indirectly from the inventor.

BACKGROUND OF THE PLANT

The present invention relates to the new and distinct threadleaf *coreopsis* herein also referred to as *Coreopsis* 'Red Hot Vanilla', by the cultivar name, 'Red Hot Vanilla', or as the new plant. The new plant was derived from seed collected in the fall of 2014 from plants in an isolation block, in a cultivated field in Zeeland, Mich., that were unreleased, proprietary, third-generation linear breeding line from 'Route 66' U.S. Plant Pat. No. 20,609, identified by the breeder code HK10-2-10. The single seedling was selected by the inventor, isolated and compared in subsequent years to other *coreopsis* and subsequently found to be different from all cultivars known to the discoverer and eventually given the breeder code 14-1-9.

Asexual propagation at the same nursery in Zeeland, Mich., USA by cuttings has shown 'Red Hot Vanilla' to be stable and reproduce true to type in successive generations.

SUMMARY OF THE PLANT

*Coreopsis* 'Red Hot Vanilla' has not been observed in all possible environmental conditions. The phenotype may vary slightly with changes in environments such as light intensity, fertility, water availability, etc. without, however any variation in genotype.

*Coreopsis* 'Red Hot Vanilla' is distinct from all cultivars known to the inventor in the following traits:

1. Narrow foliage with compact height and dense mounded habit.
2. Heavy flowering with creamy ray ligules having dark red central eye.
3. Inflorescence about 4.5 cm across with six to eight ray ligules.
4. Inflorescences produced tightly and densely above the bright-green thin foliage.
5. Long flowering period beginning with concentration in mid-June and continuing until frost.

Plants of *Coreopsis* 'Red Hot Vanilla' are most similar to 'Starlight' U.S. Plant Pat. No. 28,005, 'Balupteam' U.S. Plant Pat. No. 28,964 and 'Balupteamed' U.S. Plant Pat. No. 28,866. 'Starlight' is shorter in habit, produces wider and sterile inflorescences, has simple lanceolate foliage, the ray florets are slightly different colored. 'Balupteamed' is shorter in habit and the ray florets are deeper yellowish colored. 'Balupteam' is shorter in habit, the inflorescences are wider, and the ray florets do not have the slightly darker veins. 'Route 66' has yellowish ray florets with larger red eye of variable sizes frequently streaking toward apices.

BRIEF DESCRIPTION OF THE DRAWINGS

The color drawings illustrate the overall characteristics of *Coreopsis* 'Red Hot Vanilla' as a three-year-old plant. The colors are as true as reasonably possible given the technology available. The color values may vary slightly depending on light intensity and quality.

DETAILED BOTANICAL DESCRIPTION

Figure 1:
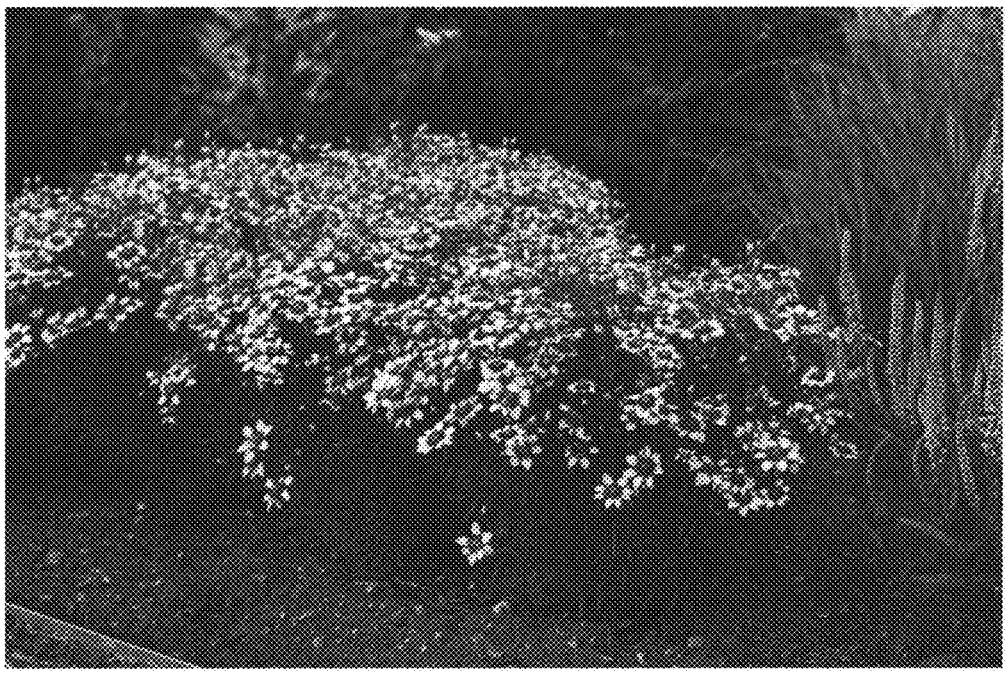
FIG. 1 shows the new plant in a landscape environment.
Figure 2:
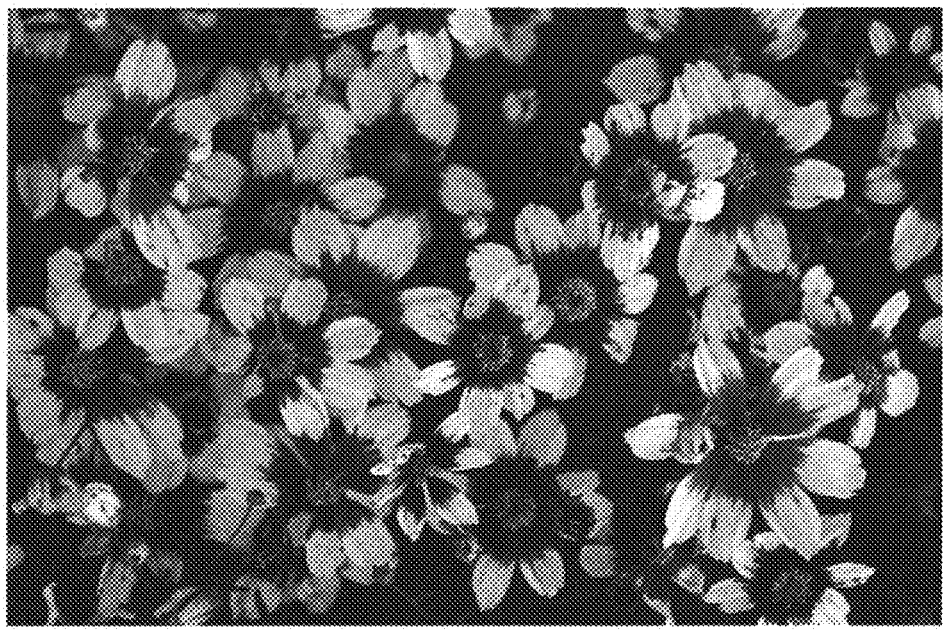
FIG. 2 shows a close-up of the flowers of the new plant.

The following description is based on a three-year-old plant growing in a full-sun trial garden in Zeeland, Mich., USA. Environmental conditions for the growing season daytime temperatures range between 12-30° C., and night temperatures range between 6-19° C. Except for ordinary dictionary color usage, color references are according to The Royal Horticultural Society Colour Chart, 2015 edition.

Parentage: Female or seed parent HK10-2-10; male or pollen parent unknown;

Asexual propagation: Cuttings, about 10 to 14 days to initiate roots; time to finish as # 1 field grown size about 9 months;

Plant habit: Dense axillary branches; rounded, herbaceous perennial mound; up to 68.0 cm wide and 46.0 cm tall; average about 65.0 cm across and about 45.0 cm tall;

Leaves: Opposite, entire, glabrous; simple lanceolate to palmate, deeply dissected, tri-lobed; acute apex; base attenuate; sessile; up to 8.0 cm long and 4.5 cm wide with individual lobes to 4.5 mm wide and 4.0 cm long, average about 4.2 cm long and 4.0 cm wide;

Leaf color: Young expanding leaves adaxial nearest RHS 137B and abaxial nearest RHS 137C; mature leaves adaxial nearest RHS N148B, abaxial nearest RHS N148C;

Veins: Pinnate; only abaxial midrib obvious;

Abaxial midrib color: Nearest RHS 137B;

Inflorescence: Radiate; composite consisting of ray and disk florets; on terminal branches; about 4.5 cm diameter, about 16.0 mm tall from lower involucral bracts to top of disk florets; attitude upright to outwardly; disk about 5 mm across;

Inflorescence fragrance: Not detected;

Phyllaries: Biseriate; outer or lower set about six to eight, acute apex, narrowly deltoid, truncate base, glabrous, to about 2.5 mm long and 0.7 mm wide at base; inner or upper set tight against ray petals, usually eight in number, about 5.0 mm long and about 1.5 mm wide, deltoid to ovate; acute apex and truncate base, Phyllary color: Lower set nearest RHS 137B with lighter margin about 0.2 mm wide of nearest RHS 160C on both adaxial and abaxial surfaces; upper set nearest RHS 146A in proximal and central portion of both abaxial and adaxial, marginally and distally nearest RHS 153C;

Flowering period: Early summer until frost, for about 18 weeks; producing over 40 flowers per stem and over 200 flowers per plant at one time;

Flower longevity: 4 to 6 days;

Flower buds: With ray florets still erect 6.0 mm wide and 9.0 mm tall, 4.0 mm across capitulum;

Flower bud color: Ray florets while still upright nearest RHS 9C distally and proximally nearest RHS 187A; phyllaries outer set nearest RHS 138A toward center and nearest RHS N144A distally and along margin; inner set base nearest RHS 146C and distally and along margin nearest RHS 152C;

Peduncle: Cylindrical; glaucous, thin, wiry, upright attitude, strong, heavily branched; 4.0 mm wide at base and 36.0 cm long; about nine nodes, average internode spacing about 4.0 cm; spacing about 2.5 cm proximally and to about 4.5 cm in the central portion;

Peduncle color: Nearest RHS 137A;

Pedicel: Cylindrical; glaucous, thin, wiry, strong; average about 0.8 mm in diameter, 3.2 cm long;

Pedicel color: Nearest RHS 137A;

Ray florets: Imperfect; staminate; typically 8 per inflorescence, rarely 6;

Ray floret ligule: Oblong elongate; apex emarginate to two-notched, margin entire; base claw, narrowly cuneate to attenuate; opening flat to form 180° angle; parallel veined; glabrous adaxial and adaxial; about 18.0 mm long and about 9.5 mm wide; basal claw about 2.0 mm long and about 0.5 mm diameter; containing only gynoecium with style about 3.0 mm long and split stigma;

*Young ray floret ligule color when first flat*.—Adaxial center between RHS 8B and RHS 8C, distally nearest RHS 8C and base nearest RHS N186C.

*Mature ray floret ligule color*.—Adaxial distally nearest RHS 13D with inner eye about 6.0 mm long nearest RHS 187B; abaxial distal half nearest RHS 4D with veins nearest RHS 4B, proximal half nearest RHS 4D with undertone of nearest RHS 187B.

*Style*.—Cylindrical; about 4.0 mm long and 0.2 mm diameter; exserted; color nearest RHS 13B; Stigma: bifid; about 1.5 mm long and 0.2 mm diameter; color nearest RHS N25C.

Disk florets: About 30 to 40 per capitulum; consisting of tepals, staminal tube and pistil; size about 6.0 mm long by 1.0 mm wide at apex;

*Tepals*.—Five, rarely four; 3.0 mm long and 0.7 mm wide, fused in the basal 2.0 mm, acute apex.

*Tepal color*.—Adaxial apex nearest RHS N45A, proximally nearest RHS N186C proximally, abaxial proximally nearest RHS 13B, distally nearest RHS N186C.

*Staminal tube*.—Made up of five, rarely four, fused stamens, about 2.0 mm long.

*Filaments*.—Cylindrical; about 1.0 mm long and 0.1 mm diameter; color nearest RHS 13B.

*Anther*.—About 1.5 mm long, nearest RHS N187A.

*Pollen*.—Fine, round, closest to RHS 13A.

*Style*.—Bifid; cylindrical; exserted; about 4.0 mm long and 0.2 mm diameter; color nearest RHS 13B.

*Stigma*.—Bifid; reflexing as it matures; about 1.5 mm long; color nearest RHS N25C.

Seed: Ellipsoidal to slightly arcuate; rounded apex and base; margin micro-erose to micro-dentate; surface glabrous; about 4.5 mm long and 2.0 mm across center;

Seed color: Variable, nearest RHS 202A;

*Coreopsis verticillata* 'Red Hot Vanilla' is tolerant of winter temperatures as low as −20° C. and summer temperatures as high as 40° C. Once established it is also tolerant of dry summer conditions but does best with ample moisture and good drainage. It is not known to be tolerant of diseases and pest that are common to other *Coreopsis* cultivars.

I claim:

1. The new and distinct cultivar of *Coreopsis* plant named 'Red Hot Vanilla' as described and illustrated and useful as a specimen landscape plant, mass planting or cut flower.

* * * * *